United States Patent [19]

Harder et al.

[11] Patent Number: 5,282,379
[45] Date of Patent: Feb. 1, 1994

[54] VOLATILE TRACERS FOR DIAGNOSTIC USE IN STEAM GENERATING SYSTEMS

[75] Inventors: Scott R. Harder, Naperville; Claudia C. Pierce, Lisle; Brian F. Post, Naperville, all of Ill.

[73] Assignee: Nalco Chemical Company, Naperville, Ill.

[21] Appl. No.: 862,964

[22] Filed: Apr. 3, 1992

[51] Int. Cl.$^5$ .............................................. G01N 31/22
[52] U.S. Cl. ...................................... 73/29.01; 422/17; 422/68.1; 436/38; 436/56
[58] Field of Search ............. 73/29.01; 422/17, 68.1; 436/38, 50, 55, 56

[56] References Cited

U.S. PATENT DOCUMENTS

| | | | |
|---|---|---|---|
| 4,783,314 | 11/1988 | Hoots et al. | 436/55 |
| 4,788,848 | 12/1988 | Hsueh | 73/29 |
| 5,006,311 | 4/1991 | Hoots et al. | 436/56 |
| 5,041,386 | 8/1991 | Pierce et al. | 436/50 |
| 5,091,108 | 2/1992 | Harder et al. | 252/188.28 |

OTHER PUBLICATIONS

Nalco Chemical Company; The Nalco Water Handbook (2nd Edition), 1988, pp. 39.47-39.48, 39.52-39.66.

Primary Examiner—Robert J. Warden
Assistant Examiner—E. Leigh Dawson
Attorney, Agent, or Firm—Joan I. Norek; Robert A. Miller; Joseph B. Barrett

[57] ABSTRACT

In a diagnostic method wherein steam condensate is evaluated, the proportion of condensate water from one steam source, versus other steam sources, is determined by adding at an addition point a tracer that is selectively carried over into the steam.

20 Claims, 3 Drawing Sheets

VOLATILE TRACERS FOR DIAGNOSTIC USE IN STEAM GENERATING SYSTEMS

TECHNICAL FIELD OF THE INVENTION

The present invention is in the technical field of diagnostic methods and agents for use in steam-generating and steam-using systems.

BACKGROUND OF THE INVENTION

Steam is a convenient form in which to transport, distribute, and supply energy, because it has a high heat content, it is fluid and thus can be divided or merged, and it may be used for its heating effect or for motive power. Steam may be used for direct heating applications such as in a thermocompressor, where high-pressure steam may be used to boost low-pressure steam to a higher pressure at which it can be used. For instance, an industrial plant may have an excess of low-pressure steam at 5 to 15 lb./in$^2$ and need 50 to 100 lb./in$^2$ steam for dryers, reboilers, or some other use where higher temperature is needed. A thermocompressor can boost the low-pressure steam to the 50 to 100 lb./in$^2$ range by using live steam directly from the boiler on the jet of the thermocompressor. When used for heating effect, however, steam is most often used for indirect applications, in which a heat transfer surface is disposed between the steam and material to be heated, such as condensors, stage heaters, process heat exchangers, reboilers, evaporators, space heaters and the like. The most common surface heat exchanger, the sheet-and-tube type, transfers heat from steam or another hot fluid to a colder fluid principally by conduction across a metal tube wall separating the two. Shell-and-tube heat exchangers can be of several designs. The more complex designs are usually more efficient, but may be more costly and more difficult to clean and maintain.

In industrial plants, large quantities of high-pressure steam are often required for a wide variety of purposes. Steam is generally generated in boilers at pressure of about 175 to 600 lb./in$^2$, and in power stations up to about 2400 lb./in$^2$, which is much higher than, for instance, the excess pressure of about 7 lb./in$^2$ in relation to the external air commonly used in low-pressure, residential steam-heating systems.

Steam employed in steam-using devices eventually condenses, and the condensate is drained or otherwise removed from the area of steam use, for instance from the heat exchange surfaces, and is collected. This is the job of the trap and subsequent condensate collection and forwarding systems. Traps vent air or other noncondensible gases, drain the condensate with a minimum of restriction, and promptly sense the presence of steam and restrict its loss from the system.

The utility industry, which is the largest energy consumer in most industrialized countries, use steam for motive power, as do many moderate-sized industrial plants that may put steam through a turbine at high pressure and then use the exhaust steam for process needs. Turbines are the major prime movers, although reciprocating piston steam engines are still found in use. In steam turbine operations the exhaust steam may be discharged to a condensor at subatmospheric pressure or into process steam headers under pressure (e.g., 100 lb./in$^2$ is common in the paper industry).

The flow of steam through a system, particularly an industrial installation, to the eventual collection of condensate, may be complex, and the steam moving through a system may be generated in a plurality of steam-generating devices, such as boilers, and steam from different boilers may take, at least in part, different routes through a system. As it passes through a system, the steam is in contact with many areas thereof, and thus its condensate may provide a great wealth of information concerning operational variations within the system. For instance, a very serious problem with process equipment is corrosion, the principal agents of which are oxygen and carbon dioxide. The impurities in the steam's condensate can disclose the existence of a corrosion problem. For instance, a drop in condensate pH may indicate an undesirable concentration of carbon dioxide in the system. Evaluation of steam condensate is an important diagnostic tool. When multiple steam-generating sources are used, however, the ability to identify the steam source would greatly improve the diagnostic method. For instance, if corrosion problems develop in fewer than all of the steam-generating sources, the ability to quantify the proportion of condensate from a given source or group of sources would be highly advantageous, particularly if there are multiple steam routes, and multiple condensate collectors. It would permit one to determine from which steam-generating sources the condensate impurity(ies) of concern were derived. A determination of the proportion of condensate from one of a plurality of steam-generating sources would also permit one to determine in turn a more accurate picture of the extent of the problem, for one would know the extent of dilution of such impurity-containing condensate with other condensate. Thus it would be highly advantageous to be able to identify steam from its generation to the collection of its condensate. It would be highly advantageous to so identify steam quantitatively. It would be highly advantageous to identify steam by a continuous monitoring system, for the purpose of determining the source of impurities and for other reasons. For instance, in a system designed so that a given condensate should contain a given proportion of condensate generated by a certain source or passing in a given amount a certain point in the system, the ability to quantitatively identify steam could be employed as a warning signal, that the amount of steam from a source or passing a point in the system has fallen off, or has risen.

In short, the ability to quantitatively identify steam moving from a given point (the steam source or other point) to a sampling point, and distinguish the condensate from that steam, or the proportion thereof, from the condensate of other steam, would greatly enhance the ability to diagnose both chemical and equipment problems in a steam-using system.

It is an object of the present invention to provide a means and method for so identifying steam, which means and method are adaptable to highly advantageous continuous monitoring systems. These and other objects of the present invention are described in more detail below.

DISCLOSURE OF THE INVENTION

The present invention provides a method of identifying the proportion of condensate water from a given steam source in a condensate water sample from a steam-using system, the proportion being related to the value of the concentration of a component in the condensate water sample. The method comprises employing as the component a tracer that is selectively carried over into steam and is sufficiently inert and sufficiently stable under the environmental and chemical conditions of the system, from its addition point to the sampling point, at the dosage of the component used. The method includes the steps of adding the component at an addition point in known initial concentration ($C_I$), sampling the fluid of the system at the sampling point, and sensing a characteristic of the tracer in the condensate water sample that is proportional to its concentration in the condensate water sample ($C_F$). The sensed characteristic is then converted to the $C_F$ value, and the ratio of $C_F/(C_I-C_D)$ is determined, wherein $C_D$ is the amount of the component normally decharacterized in the system between the addition point and the sampling point, in terms of concentration of the component. The characteristic of the tracer is one of emissivity, absorbance, voltammetricity, or potentiometricity.

PREFERRED EMBODIMENTS OF THE INVENTION

Steam generating and steam-using systems are often routinely monitored to detect corrosion problems and/or monitor the effectiveness of a corrosion prevention program. The sampling is often done at the significant points of the system, and generally with quills installed in the lines that project into the flowing stream so that the water samples are not taken close to pipe walls. The pH and conductivity of a sample are routinely determined. A sample often is tested for carbon dioxide content and hardness. Test nipples may be installed in steam or condensate lines to permit both visual inspection of system conditions and as a measure of corrosion. Test coupons are used to evaluate condensate corrosion conditions. The concentration of corrosion products, such as iron and copper, in condensate is a widely used means for determining corrosion trends. These and other measurements may be severely diminished as diagnostic means when the condensate or water sample is a mixture as to the source of the steam from which they are derived. As mentioned above, if the sample being evaluated has multiple steam sources (steam which was produced at different boilers or which has taken different routes), and the problem exists in less than all boilers, or along less than all routes, a precise determination of each boiler's or route's contribution of condensate to the sample is needed. It is believed that before the present invention there has existed no reasonable means for identifying steam and its condensate, and for determining such contributions.

The tracer of the present invention must be a substance that is vaporized in a steam-generating device, such as a boiler, or at another point(s) in a system, so as to be selectively carried over into the steam. The tracer thus must have a reasonable degree of volatility. The tracer must have a reasonably high degree of stability at the high temperatures of steam-generating and/or steam-using systems, and be substantially inert under use conditions at the recommended dosages. The tracer preferably should be easy to feed to the system at all desired feed points and at the recommended dosages. The tracer should be easy to detect with precision and accuracy, and preferably by a means that can be used on a continuous basis, with a short assay time. The tracer should also be a substance that will be distributed to specific condensate waters in a determinable proportion to the steam source ("source" in the sense of the steam from which the condensate is derived) in question.

The tracer of the present invention should have sufficient volatility for selective carry over into the steam of a steam-using device. Such selective carry over does not require that all, or at times even most, of the initial concentration of the tracer at the addition point be carried over into the steam in proportion to its concentration at the addition point. Instead, for a given initial concentration of tracer a determinable and substantially constant percentage of tracer should be carried over into the steam under the operating conditions of a system, so that a determinable relationship between the concentration of the tracer in the condensate of a given addition point, versus the initial concentration of the tracer at such addition point, can be established. Substances of high volatility, for instance substances having a vapor/liquid ($V/L''$) ratio of from about 1 to about 10, or 15, or higher, are preferred, but such high volatility is not essential. Such highly volatile substances may be employed at low concentrations, because a proportionately high concentration thereof will be present in the condensate, and it is possible that the relationship between addition point concentration and condensate concentration may be more stable for high volatility substances. Nonetheless, since the assay methods available for the present invention in instances may detect accurately concentrations of some substances down to levels of a few parts per billion by weight ("ppb"), a substance that has a V/L of for instance 0.1, or 0.2, may be required in only a few parts per million by weight ("ppm") concentration at the addition point to be readily and accurately detectable in the condensate. A substance of less than high volatility may, in instances, be preferred for reasons other than volatility, for instance for its stability under use conditions, or its detectability against the background characteristics of the condensate.

The tracer should be stable and substantially inert under the use conditions at the recommended dosages. As will be discussed below concerning some specific tracer substances examples, it is not essential that the tracer be wholly inert under use conditions. For instance, if a tracer reacts with a certain specie that may be present in some steam-using systems, and such reaction decharacterizes the molecules that enter into such reaction, an appropriate dosage of the tracer substance would be sufficiently high so that $C_I-C_D$ is greater than zero. That is, the amount of substance lost by virtue of a decharacterizing reaction, represented by the value of $C_D$, must be less than the initial concentration, $C_I$, provided by the dosage.

A decharacterizing reaction is not the sole phenomenon resulting in a $C_D$ value other than zero. For instance, a tracer may have some predictable decharacterizing instability that is dependent upon, for instance, its residence time at the addition point, and such loss may be, in instances, be best accounted for using an appropriate non-zero value for $C_D$.

In some systems, and/or under some circumstances, a decharacterizing loss of tracer substance may be balanced not by use of a non-zero value for $C_D$, but instead by offsetting the loss in the feed of the substance at the addition point by an initial charge of the substance that is not included in the $C_I$ value.

The tracer should be preferably be fed to the addition point as an aqueous solution or aqueous dispersion, and such solution or dispersion should be sufficiently fluid so as to disperse through the waters of the system at such addition point easily under normal operating conditions at the addition point.

In preferred embodiment, the addition point of the steam-using system is the main steam-generating system, or boiler, or one or more of a plurality of boilers in a steam-using system. In such preferred embodiment the method of the present invention would find its most common, and possibly most immediately important use, as a diagnostic method for a steam-using system that has a plurality of boilers wherein a given tracer is employed in less than all of such boilers, to distinguish the condensate of one or more boilers from that of one or more boilers having no tracer or having different tracer substances.

The Assay Methods

In general, the assay method determines the amount of a tracer by the intensity or strength of the characteristic being measured, which can be converted to a concentration equivalent. If the tracer employed is fluorescent, the use of its fluorescence emissivity characteristic, measured on a fluorometer, would be particularly useful. Fluorescent tracers may be selectively detectable down to very low concentrations, and emissivity generally can be converted to analog. Concentrations of fluorescent tracers required for purposes of the present invention generally will not contribute significantly to conductivity, which is advantageous in steam-using systems. There are invariably some background interferences, such as natural fluorescence in the condensate. If such natural fluorescent creates a significant interference for the same excitation/emission wavelengths desired to be used for detecting a given tracer, such interference may be overcome or sufficiently diminished by increasing the use concentration of the tracer, or employing a different excitation/emission wavelength set or a different tracer.

Figure 1:
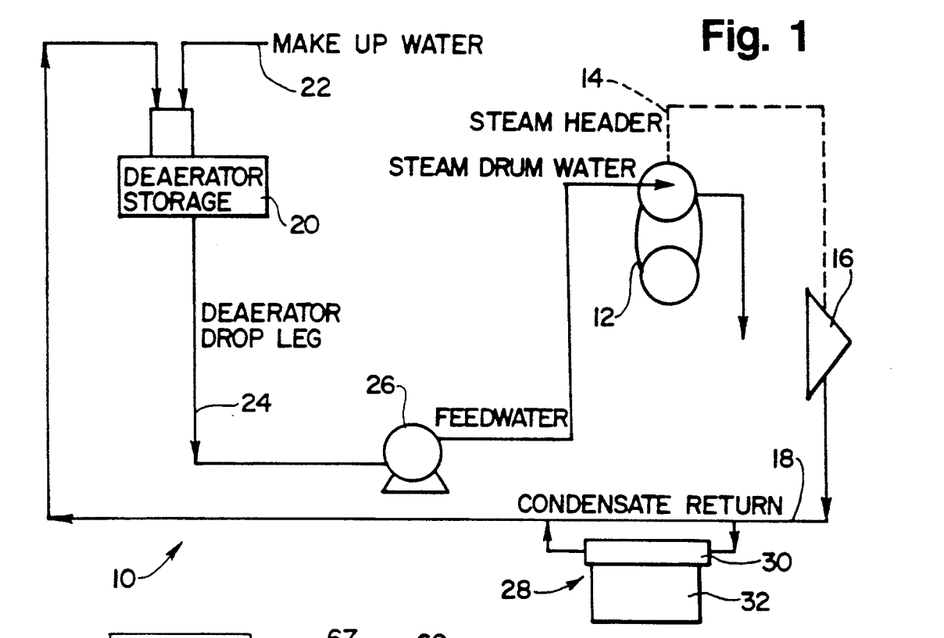
FIG. 1 is a schematic drawing of a steam-using system generally and instrumentation for continuous monitoring of tracer concentration generally.

For any assay method, it is generally preferred that the monitoring be conducted on a continuous basis, rather than an intermittent or batch basis. As shown in FIG. 1, a steam-using system can be depicted generally by a schematic, the system overall being designated by the reference number 10. The system 10 is generally comprised of at least one boiler 12, steam header 14, steam-use zone 16, condensate return system 18, deaerator storage 20 (receiving water from both the condensate return system 18 and a make-up water system 22), a deaerator drop leg 24, and a feed water zone 26. Also shown schematically in FIG. 1 is the instrumentation 28 for continuous monitoring of the concentration of the tracer in the condensate. Such instrumentation 28 includes, as major components, a sensor or detector 30 for determining from an on-stream characteristic of the tracer its concentration in the sample, including a transducer which generates an electronic signal (voltage) corresponding to that analysis and an output recording device or other register 32 that generates a continuous record of the concentration analog of the tracer as a function of time.

Figure 2:
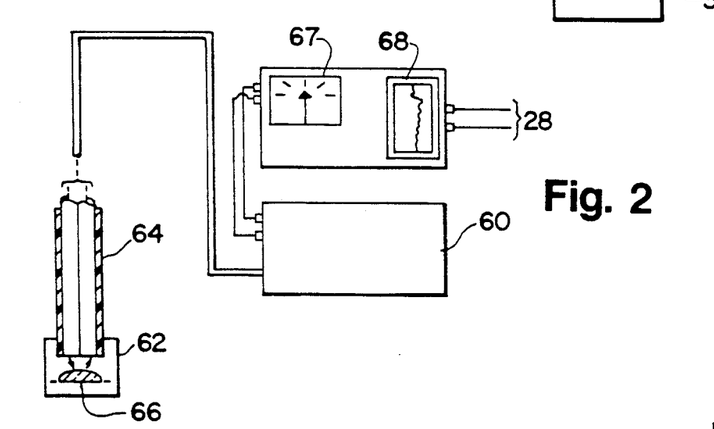
FIG. 2 is a schematic drawing of spectrophotometry instrumentation.

Colorimetry or spectrophotometry may be employed for a tracer such as a dye, in which event the voltage concentration analog is based on absorbance values rather than fluorescent emissivity. A schematic arrangement is shown in FIG. 2. The sample solution is admitted to a flow cell 62 in which a fiber optic dual probe 64 is immersed. One fiber optic cable shines incident light through the sample on to a mirror 66 inside the cell and reflected light is transmitted back through the sample liquid into a fiber optic cable and then to the colorimetric analyzer unit by the other cable as shown by arrows. The colorimeter 60 has a transducer which develops an electric analog signal of the reflected light characteristic of the tracer concentration. The voltage emitted by the transducer activates a dial indicator 67 and a continuous line recorder printout unit 68.

An ion selective electrode may be employed to determine the concentration of a tracer ion in terms of the relationship between the electrical signal developed by the electrode and the concentration of tracer. By calibration (potential or current versus concentration) the ionic concentration at the sample electrode can be indexed to a reference (standard) electrode which is insensitive to the tracer ion. To provide continuous monitoring of the tracer ion, the electrodes may be dipped directly into a flowing stream of the sample, collectively constituting a flow cell, or the sample could be passed through an internal flow cell into which the ion-selective and reference electrodes have been inserted.

Figure 3:
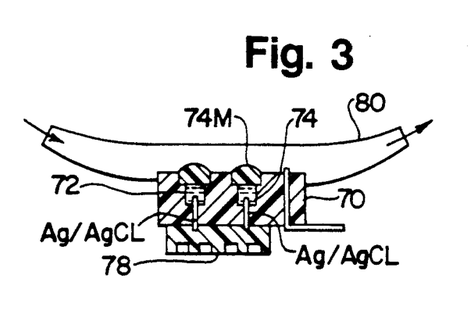
FIG. 3 is a schematic drawing of an ion selective electrode system.
Figure 4:
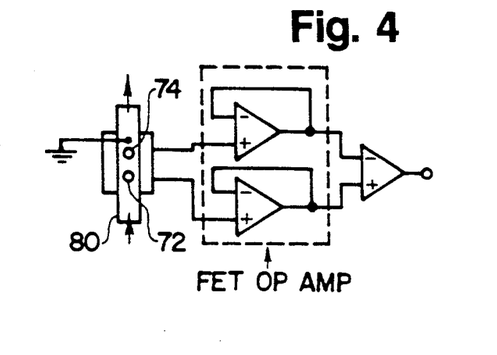
FIG. 4 is a schematic drawing of a ion selective flow cell.

An example of a flow cell incorporating an ion selective electrode system is shown in FIG. 3, comprising a polyvinyl chloride sensor base or module 70 containing the reference and sample electrodes (cells) respectively denoted 72 and 74, each including a silver/silver chloride electrode wire, and a grounding cell across which a potential develops proportional to the logarithm of the activity of the selected ion. An eight pin DIP socket 78 will be wired to a stand dual FET ("field effect transistor") op amp device. The sample is conducted across the electrodes by a flexible tube 80. The tracer ions penetrate only the sample (ion selective) electrode cell 74. The FET op amp device (a dual MOSFET op amp) is thus connected to the flow cell shown in FIG. 4 to perform the impedance transformation, whereby the potential difference between the reference and sample electrodes may be obtained, using an amplifier. The transducer is in effect the ionophore membrane 74M of the sample electrode allowing the selected ion activity (concentration) to be transformed to a weak voltage which when amplified can be monitored between setpoints.

The following description of substances that may be employed as tracers in the method of the present invention is not an exhaustive list of potential tracers. Instead such description illustrates the existence of suitable substances for the purposes of the present invention, and as to certain preferred embodiments provides a more detailed description of the properties of such substances, and suitable assay method that may be used to determine a characteristic of such substance that is proportional to the concentration of such substance in steam condensate.

N,N,N,N-tetra Substituted Phenylenediamines

The N,N,N,N-tetra substituted phenylenediamine, which have volatility ratios that provide selective carry over into steam sufficient for the purposes of the present invention, are described in U.S. Pat. No. 5,091,108, Harder, et al., issued Feb. 25, 1992, which is incorporated hereinto by reference. They have volatilities such that a high vapor/liquid, or V/L, ratio is obtained when these compounds are fed to an operating boiler or similar addition point in a steam-using system. They advantageously provide no contribution to dissolved solids in high pressure boiler systems operating at temperatures ranging from 250° F. to about 900° F., or above. These compounds advantageously have low toxicity, and can easily be formulated in aqueous based solutions, either soluble or dispersed as need be. They are generally available at reasonable cost.

One such N,N,N,N-tetra substituted phenylenediamine, namely N,N,N,N-tetramethyl phenylenediamine ("TMPD") is highly volatile, and has a demonstrated V/L ratio in the 2-8 V/L ratio range. It has a toxicity that is less than hydroquinone, and less than unsubstituted phenylene diamine.

The N,N,N,N-tetra substituted phenylenediamines are exemplitive of components wherein the $C_D$ value is generally greater than one, because, as is discussed in aforesaid U.S. Pat. No. 5,091,108, the N,N,N,N-tetra substituted phenylenediamines are oxygen scavengers, and when oxygen is present in the waters of a system, the N,N,N,N-tetra substituted phenylenediamine dosage must be greater than the stoichiometric amount of N,N,N,N-tetra substituted phenylenediamine consumed in the oxygen scavenging process. That amount consumed in oxygen scavenging could be accounted for in the present method by charging the stoichiometry amount needed for oxygen scavenging before charging the initial dosage which is used to calculate the proportion of condensate water in question. Alternatively, the amount consumed in oxygen scavenging can be deemed, for purposes of the present invention, the amount that is decharacterized.

Useful N,N,N,N-tetra substituted phenylenediamine for the purposes of the present invention include compounds having the structure set forth in Formula I Formula I wherein $R_1$, $R_2$, $R_3$ and $R_4$ are independently linear or branched alkyl groups having from 1 to 4 carbon atoms, carboxylate alkyl groups having from 1 to 4 carbon atoms, or radicals represented by the structure:

wherein n is a number from about 1 to about 3, and M is hydrogen, an alkali metal cation, an alkaline earth metal cation, ammonium cation, acidified or quaternized amino cation, mixtures thereof, and equivalent cationic species present in electroneutralizing amounts. The N,N,N,N-tetra substituted phenylenediamines of Formula I that include carboxylate groups are advantageously water soluble to a greater degree than their alkyl-substituted counterparts (the N,N,N,N-tetra substituted phenylenediamines resultant upon decarboxylation) and hence are readily feed to a boiler system. Such carboxylate-containing N,N,N,N-tetra substituted phenylenediamines, however, are believed to undergo decarboxylation in the environment of a typical boiler. In those circumstances where a carboxylate containing N,N,N,N-tetra substituted phenylenediamine is added to a steam-using system, and the specie that is carried over into the steam is the decarboxylated specie, the decarboxylated specie is considered added to the system by the addition of such carboxylated precursor. Specific examples of these N,N,N,N-tetra substituted phenylenediamines, including precursors, as to combinations of their respective $R_1$, $R_2$, $R_3$ and $R_4$ groups, are identified thereby in Table 1 below.

TABLE 1

| Example No. | $R_1$ | $R_2$ | $R_3$ | $R_4$ |
|---|---|---|---|---|
| 1 | $CH_3$ | $CH_3$ | $CH_3$ | $CH_3$ |
| 2 | $(CH_3)_3C$ | $CH_3$ | $CH_3$ | $CH_3$ |
| 3 | $C_2C(O)OH$ | $C_2C(O)OH$ | $C_2C(O)OH$ | $C_2C(O)OH$ |
| 4 | $C_2C(O)OH$ | $CH_3$ | $C_2C(O)OH$ | $C_2C(O)OH$ |
| 5 | $C_2C(O)OH$ | $CH_3$ | $CH_3$ | $C_2C(O)OH$ |
| 6 | $C_2C(O)OH$ | $CH_3$ | $CH_3$ | $CH_3$ |
| 7 | $C_2C(O)OH$ | $CH_3$ | $C(CH_3)_3$ | $CH_3$ |
| 8 | $CH_3CH_2$ | $C_2C(O)OH$ | $CH_3$ | $CH_2CH(CH_3)_2$ |
| 9 | $CH_3$ | $CH_3$ | $C_2C(O)OH$ | $C_2C(O)OH$ |
| 10 | $CH_3$ | $C_2H_5$ | $CH(CH_3)_2$ | $C_2C(O)OH$ |

As described in the above noted U.S. Pat. No. 5,091,108, the N,N,N,N-tetra substituted phenylenediamines are effective oxygen scavengers advantageously employed in steam-using systems to remove oxygen not only from the boiler)s) of the system but also, because they selectively carry over into the steam, from the condensate system. In the method of the present invention, if such a system required the use of an oxygen scavenger, the N,N,N,N-tetra substituted phenylenediamine of choice would be employed in an amount in excess of that required for oxygen removal. TMPD is not only a preferred oxygen scavenger, as noted in U.S. Pat. No. 5,091,108, it is also a preferred tracer substance for the method of the present invention.

Figure 5:
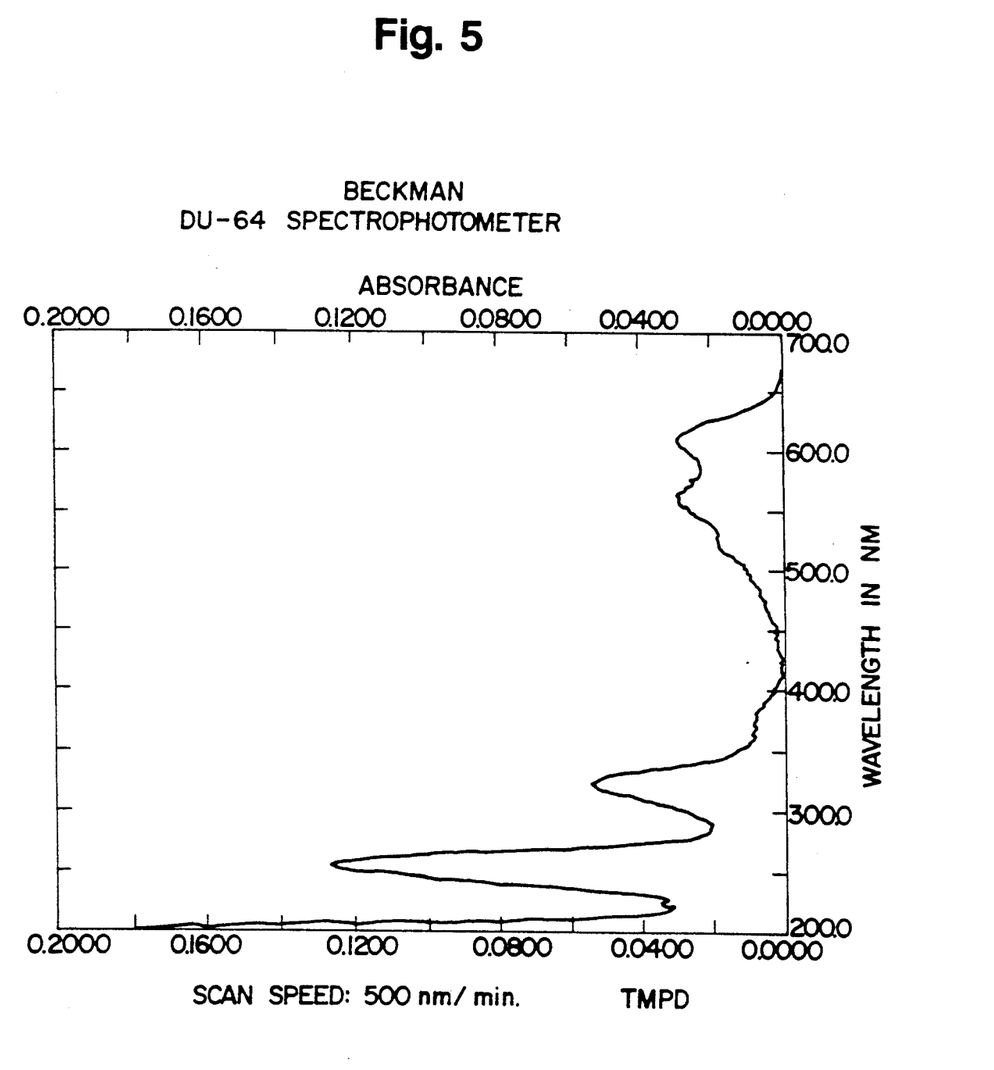
FIG. 5 is a spectrophotometric absorbance spectra of a tracer.

It is believed that most of the N,N,N,N-tetra substituted phenylenediamine compounds are detectable using absorbance. For instance, TMPD oxidizes by one electron to produce an intensely blue color, and as shown in FIG. 5, and the absorbance of such oxidized TMPD is readily determined using a spectrophotometer in the visible wavelength range. TMPD and other N,N,N,N-tetra substituted phenylenediamine compounds are also advantageously stable under the high temperature and pressure conditions of even the modern high pressure boilers.

Although the unsubstituted phenylenediamine is not considered sufficiently volatile to be an effective oxygen scavenger both for a boiler, and by selective carry over into the steam for the condensate system, its volatility (a V/L ratio of about 0.1 to about 0.2) may be sufficient for its use as a tracer in the present invention. The concentration of such substance in the condensate need not be sufficient for corrosion protection, but instead only sufficient for detectability.

The Substituted Quinolines

The substituted quinoline compounds are another class of substances that generally provide selective carry over into steam sufficient for the purposes of the present invention. They also generally provide no contribution to dissolved solids in even high pressure boiler systems. These compounds can easily be formulated in aqueous based solutions, either soluble or dispersed as need be, and they are generally available at reasonable cost. They are generally stable under even the high pressure and temperature conditions of modern high pressure boilers.

Figure 6:
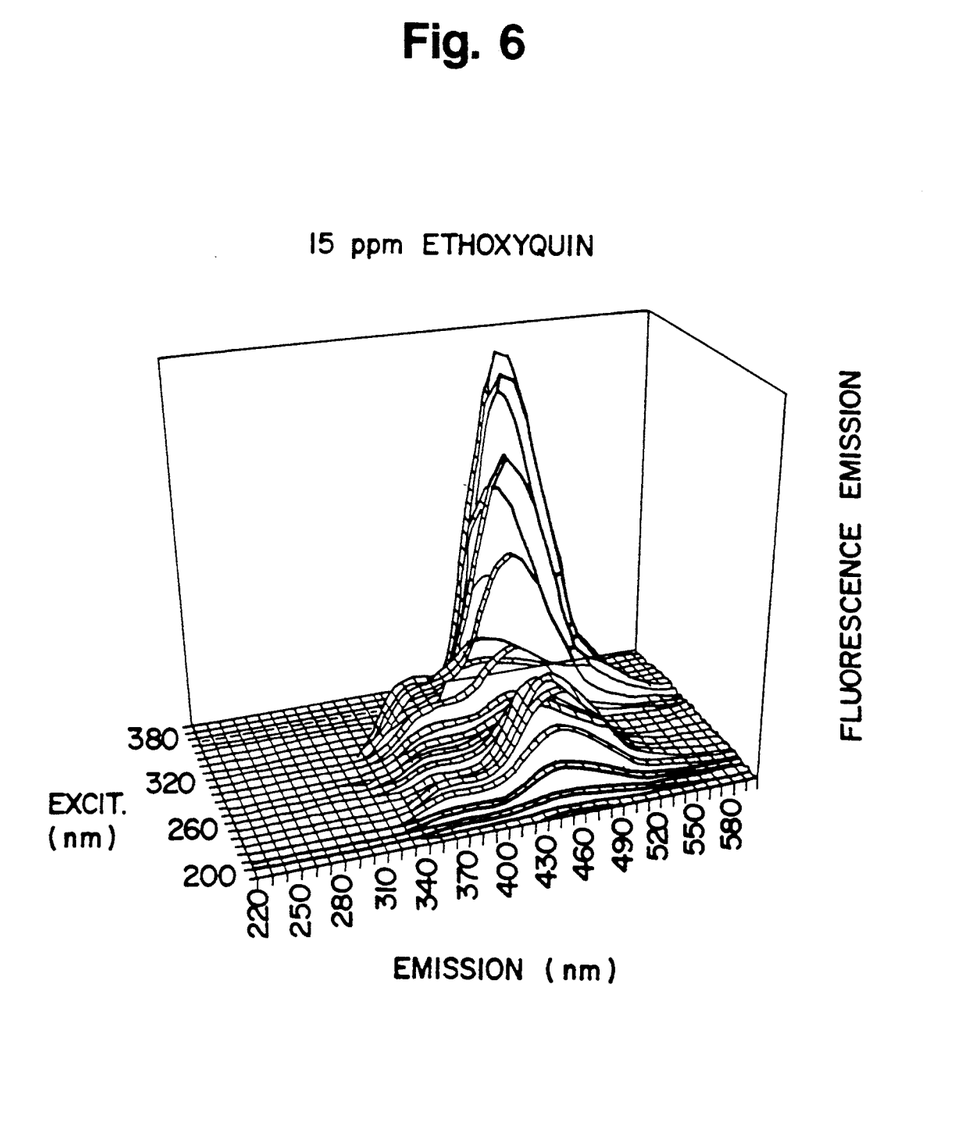
FIG. 6 is a three-dimensional fluorescence spectra of a tracer.

One such quinoline, namely ethoxyquin, is highly volatile and has a V/L ratio of from about 3 to about 6. Ethoxyquin is readily detectable by fluorescence. A three dimensional fluorescence spectra of ethoxyquin, in aqueous solution at a concentration of 15 ppm, is shown in FIG. 6, for excitation wavelengths ranging from about 200 to about 380 nanometers ("nm") and emission wavelengths of from about 220 to about 580 nm. Distinct fluorescence emission peaks in the emission wavelength range of from about 400 to 520 nm are seen.

Useful quinoline compounds for the purposes of the present invention include compounds having the structure set forth in Formula II Formula II wherein $R_5$, $R_6$, $R_7$, $R_8$, and $R_9$ are each independently hydrogen, linear or branched alkyl groups each having from 1 to 4 carbon atoms, alkoxylated groups having from one to 6 carbon atoms, or radicals represented by the structure:

wherein n is a number from about 1 to about 3, and M is hydrogen, an alkali metal cation, an alkaline earth metal cation, ammonium cation, acidified or quaternized amino cation, mixtures thereof, and equivalent cationic species present in electroneutralizing amounts.

The preferred ethoxyquin compound has the structure of Formula II above wherein $R_5$ is the two carbon atom ethoxy radical ($CH_3CH_2O$), $R_6$ is hydrogen, and each of $R_7$, $R_8$, and $R_9$ are methyl ($CH_3$).

The Quinazolines

Quinazoline and the substituted quinazoline compounds are another class of substances that generally provide selective carry over into steam sufficient for the purposes of the present invention. They also generally provide no contribution to dissolved solids in even high pressure boiler systems. These compounds can easily be formulated in aqueous based solutions, generally soluble, but dispersed if need be, and they are generally available at reasonable cost. They are generally stable under even the high pressure and temperature conditions of modern high pressure boilers. These compounds also generally are easily detectable by fluorescence emission.

Quinazoline has the structure set forth in Formula III

Formula III

The substituted quinazolines are generally compounds having the heterocyclic quinazoline structure shown in Formula III above, substituted by linear or branched alkyl groups having from 1 to 4 carbon atoms, or alkoxylated groups having from one to 6 carbon atoms, or radicals represented by the structure:

wherein n is a number from about 1 to about 3, and M is hydrogen, an alkali metal cation, an alkaline earth metal cation, ammonium cation, acidified or quaternized amino cation, mixtures thereof, and equivalent cationic species present in electroneutralizing amounts and combinations of such substituents.

Industrial Applicability of the Invention

The present invention is applicable to the numerous industries that generate and/or use steam, regardless of whether such steam is used for motive power or for heating purposes or for both.

We claim:

1. A method of identifying the proportion of steam condensate water from a given steam source in a condensate water sample from a steam-using system comprising:
   adding a tracer to a steam source of a steam-using system having condensate water at an addition point in known initial concentration ($C_I$);
   sampling the condensate water of said steam-using system at a sampling point;
   sensing a characteristic of said tracer in said condensate water sample that is proportional to the concentration of said tracer in said condensate water sample ($C_F$);
   converting said sensed characteristic to said $C_F$ value;
   determining the ratio of $C_F/(C_I-C_D)$, wherein $C_D$ is the amount of said tracer decharacterized as to said characteristic in said system between said addition point and said sampling point, in terms of concentration of said tracer,
   wherein said tracer is a chemical species sufficiently selectively carried over into the steam of said steam source to provide a concentration $C_F$ sufficient to enable said sensing of said characteristic;
   wherein $C_D$ is less than $C_I$; and
   wherein said ratio of $C_F/(C_I-C_D)$ is an indicator of the proportion of steam condensate water from a given steam source in a condensate water sample from a steam-using system.

2. The method of claim 1 wherein said characteristic of said tracer is one of emissivity, absorbance, voltammetricity, or potentiometricity.

3. The method of claim 1 wherein said system includes a water-containing water-feeder, a water-containing boiler, or a water-containing steam header, and said addition point is said water-feeder, said boiler or said steam header.

4. The method of claim 1 wherein said tracer is fluorescent and the sensed characteristic of said tracer is said tracer's fluorescence emissivity.

5. The method of claim 1 wherein said sensed characteristic of said tracer is its absorbance in the visible or ultraviolet wavelength ranges.

6. The method of claim 1 wherein said steam-using system has a plurality of boilers, and
said addition point is at one or more, but less than all, of said boilers.

7. The method of claim 1 wherein said tracer is an N,N,N,N-tetra substituted phenylenediamine.

8. The method of claim 1 wherein said tracer is N,N,N,N-tetramethyl phenylenediamine.

9. The method of claim 1 wherein said tracer is a substituted quinoline.

10. The method of claim 1 wherein said tracer is ethoxyquin.

11. The method of claim 1 wherein said tracer is quinazoline.

12. The method of claim 1 wherein said tracer is a substituted quinazoline.

13. The method of claim 1 wherein $C_I$ is monitored on a continuous basis.

14. The method of claim 1 wherein said tracer has a vapor/liquid ratio of at least about 1.0.

15. A method of determining the source of a substance in steam condensate waters wherein more than one source of steam contributes condensate to said steam condensate waters, comprising:
adding a tracer to at least one, but less than all, of a plurality of sources of steam
at an addition point in known initial concentration ($C_I$);
wherein said plurality of sources of steam each contribute condensate to steam condensate waters;
sampling said steam condensate waters at a sampling point;
sensing a characteristic of said tracer in said steam condensate water sample that is proportional to the concentration of said tracer in said condensate water sample ($C_F$);
converting said sensed characteristic to said $C_F$ value;
determining the ratio of $C_F/(C_I-C_D)$, wherein $C_D$ is the amount of said tracer decharacterized as to said characteristic between said addition point and said sampling point, in terms of concentration of said tracer.
wherein said tracer is a chemical species sufficiently selectively carried over into the steam of said steam source to provide a concentration $C_F$ sufficient to enable said sensing of said characteristic;
wherein $C_D$ is less than $C_I$, and
wherein said ratio of $C_F/(C_I-C_D)$ is an indicator of the proportion of steam condensate water from a given steam source in a condensate water sample from a steam-using system.

16. The method of claim 15 wherein said characteristic of said tracer is one of emissivity, absorbance, voltammetricity, or potentiometricity.

17. The method of claim 15 wherein said tracer is fluorescent and the sensed characteristic of said tracer is said tracer's fluorescence emissivity.

18. The method of claim 15 wherein said sensed characteristic of said tracer is its absorbance in the visible or ultraviolet wavelength ranges.

19. The method of claim 15 wherein said tracer is N,N,N,N-tetramethyl phenylenediamine.

20. A method of identifying the proportion of steam condensate water from a given steam source in a condensate water sample from a steam-using system comprising:
adding a tracer to a steam source of a steam-using system having condensate water at an addition point in known initial concentration ($C_I$);
sampling the condensate water of said steam-using system at a sampling point;
sensing a characteristic of said tracer in said condensate water sample that is proportional to the concentration of said tracer in said condensate water sample ($C_F$);
converting said sensed characteristic to said $C_F$ value;
determining the ratio of $C_F/(C_I-C_D)$, wherein $C_D$ is the amount of said tracer decharacterized as to said characteristic in said system between said addition point and said sampling point, in terms of concentration of said tracer,
wherein said tracer is a chemical species sufficiently selectively carried over into the steam of said steam source to provide a concentration $C_F$ sufficient to enable said sensing of said characteristic;
wherein $C_D$ is less than $C_I$,
wherein said ratio of $C_F/(C_I-C_D)$ is an indicator of the proportion of steam condensate water from a given steam source in a condensate water sample from a steam-using system; and
wherein said tracer is an N,N,N,N-tetra substituted phenylenediamine, a substituted quinoline, a quinazoline, or a substituted quinazoline.

* * * * *

UNITED STATES PATENT AND TRADEMARK OFFICE
CERTIFICATE OF CORRECTION

PATENT NO. : 5,282,379
DATED : February 1, 1994
INVENTOR(S) : Scott R. Harder, et al It is certified that error appears in the above-indentified patent and that said Letters Patent is hereby corrected as shown below:

Column 12, Line 3, Claim 15 wherein $C_D$ is less than $C_r$ and

LETTERS PATENT SHOULD READ AS:

wherein $C_D$ is less than $\underline{C_I}$; and

Column 12, Line 42, Claim 20 wherein $C_D$ is less than $C_r$,

LETTERS PATENT SHOULD READ AS:

wherein $C_D$ is less than $\underline{C_I}$;

Signed and Sealed this

Twenty-first Day of June, 1994

Attest:

BRUCE LEHMAN

Attesting Officer    Commissioner of Patents and Trademarks